US010272225B2

(12) United States Patent
Bathe et al.

(10) Patent No.: US 10,272,225 B2
(45) Date of Patent: *Apr. 30, 2019

(54) GAS DELIVERY DEVICE AND SYSTEM

(71) Applicant: Mallinckrodt Hospital Products IP Limited, Dublin (IE)

(72) Inventors: Duncan Bathe, Fitchburg, WI (US); John Klaus, Cottage Grove, WI (US); David Christensen, Cambridge, WI (US)

(73) Assignee: Mallinckrodt Hospital Products IP Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 15/001,020

(22) Filed: Jan. 19, 2016

(65) Prior Publication Data

US 2016/0136377 A1 May 19, 2016

Related U.S. Application Data

(63) Continuation of application No. 14/065,962, filed on Oct. 29, 2013, now Pat. No. 9,265,911, which is a (Continued)

(51) Int. Cl.
*A61M 16/20* (2006.01)
*A61M 16/00* (2006.01)
(Continued)

(52) U.S. Cl.
CPC ...... *A61M 16/202* (2014.02); *A61M 16/0051* (2013.01); *A61M 16/024* (2017.08);
(Continued)

(58) Field of Classification Search
CPC .. A61M 5/168; A61M 5/16831; A61M 5/172; A61M 16/10; A61M 16/20;
(Continued)

(56) References Cited

U.S. PATENT DOCUMENTS 4,308,865 A 1/1982 Hay
4,462,398 A 7/1984 Durkan et al.
(Continued)

FOREIGN PATENT DOCUMENTS

FR 2917804 A1 12/2008
JP 2009-545337 A 12/2009

OTHER PUBLICATIONS

PCT International Search Report and Written Opinion for PCT/US2011/020319, dated Jan. 31, 2012.
(Continued)

*Primary Examiner* — Michael J Tsai

(57) ABSTRACT

A gas delivery system including a gas delivery device, a control module and a gas delivery mechanism is described. An exemplary gas delivery device includes a valve assembly with a valve and circuit including a memory, a processor and a transceiver in communication with the memory. The memory may include gas data such as gas identification, gas expiration and gas concentration. The transceiver on the circuit of the valve assembly may send wireless optical line-of-sight signals to communicate the gas data to a control module. Exemplary gas delivery mechanisms include a ventilator and a breathing circuit. Methods of administering gas are also described.

18 Claims, 12 Drawing Sheets

Related U.S. Application Data continuation of application No. 13/509,873, filed as application No. PCT/US2011/020319 on Jan. 6, 2011, now Pat. No. 8,573,209.

(51) Int. Cl.

| | | |
|---|---|---|
| A61M 16/12 | (2006.01) | |
| A61M 16/10 | (2006.01) | |
| A61M 16/08 | (2006.01) | |
| A61M 16/04 | (2006.01) | |
| A61M 16/06 | (2006.01) | |
| A61M 16/16 | (2006.01) | |

(52) U.S. Cl.
CPC ........ *A61M 16/04* (2013.01); *A61M 16/0666* (2013.01); *A61M 16/085* (2014.02); *A61M 16/0875* (2013.01); *A61M 16/104* (2013.01); *A61M 16/1005* (2014.02); *A61M 16/12* (2013.01); *A61M 16/20* (2013.01); *A61M 16/204* (2014.02); *A61M 16/208* (2013.01); *A61M 16/0808* (2013.01); *A61M 16/0833* (2014.02); *A61M 16/16* (2013.01); *A61M 2016/0027* (2013.01); *A61M 2016/0039* (2013.01); *A61M 2016/102* (2013.01); *A61M 2016/1025* (2013.01); *A61M 2016/1035* (2013.01); *A61M 2202/0208* (2013.01); *A61M 2202/0233* (2013.01); *A61M 2202/0266* (2013.01); *A61M 2202/0275* (2013.01); *A61M 2202/0283* (2013.01); *A61M 2205/18* (2013.01); *A61M 2205/27* (2013.01); *A61M 2205/3327* (2013.01); *A61M 2205/3334* (2013.01); *A61M 2205/35* (2013.01); *A61M 2205/3561* (2013.01); *A61M 2205/3569* (2013.01); *A61M 2205/3592* (2013.01); *A61M 2205/50* (2013.01); *A61M 2205/502* (2013.01); *A61M 2205/52* (2013.01); *A61M 2205/60* (2013.01); *A61M 2205/6009* (2013.01); *A61M 2205/6072* (2013.01); *A61M 2205/8206* (2013.01); *A61M 2209/084* (2013.01); *F17C 2205/013* (2013.01); *F17C 2205/0161* (2013.01); *F17C 2205/0308* (2013.01); *F17C 2205/05* (2013.01); *F17C 2205/054* (2013.01); *F17C 2221/01* (2013.01); *F17C 2221/011* (2013.01); *F17C 2250/032* (2013.01); *F17C 2270/02* (2013.01)

(58) Field of Classification Search
CPC .............. A61M 16/00; A61M 2205/14; A61M 2205/276; A61M 2205/3546; A61M 2205/3553; A61M 2205/3561; A61M 2205/3569; A61M 2205/60; A61M 2205/0072; A61M 2205/6081; A61M 16/122; A61M 2016/1005; A61M 2016/102; A61M 2016/1025; A61M 2016/103; A61M 2016/1035; A61M 2016/20; A61M 2016/201; A61M 2016/202; A61M 16/203; A61M 16/204; A61M 16/205; F17C 2205/05; F17C 2205/054; F17C 2205/057; F17C 2205/058; F17C 13/003; F17C 2250/03; F17C 2250/032; F17C 2250/034; F17C 2250/036; F17C 2270/02; F17C 2270/025; A62B 9/00; A62B 18/00
See application file for complete search history.

(56) References Cited

U.S. PATENT DOCUMENTS

| | | | |
|---|---|---|---|
| 5,078,683 A | 1/1992 | Sancoff et al. | |
| 5,100,380 A | 3/1992 | Epstein et al. | |
| 5,191,317 A | 3/1993 | Toth et al. | |
| D339,635 S | 9/1993 | Waterson et al. | |
| 5,440,477 A | 8/1995 | Rohrberg et al. | |
| 5,485,827 A | 1/1996 | Zapol et al. | |
| 5,505,195 A | 4/1996 | Wolf et al. | |
| 5,558,083 A | 9/1996 | Bathe et al. | |
| 5,732,693 A | 3/1998 | Bathe et al. | |
| 5,752,504 A | 5/1998 | Bathe | |
| 5,794,645 A | 8/1998 | Rohrberg et al. | |
| 5,868,162 A | 2/1999 | Dickerson, Jr. | |
| 5,913,309 A | 6/1999 | Sheehan et al. | |
| 6,089,229 A | 7/2000 | Bathe et al. | |
| 6,109,260 A | 8/2000 | Bathe | |
| 6,125,846 A | 10/2000 | Bathe et al. | |
| 6,164,276 A | 12/2000 | Bathe et al. | |
| 6,221,051 B1* | 4/2001 | Hjertman .............. | A61M 5/145 128/DIG. 1 |
| 6,326,896 B1 | 12/2001 | McDermott et al. | |
| 6,581,592 B1 | 6/2003 | Bathe et al. | |
| D483,859 S | 12/2003 | Omholt | |
| 6,811,533 B2 | 11/2004 | Lebel et al. | |
| D510,044 S | 9/2005 | Ribeiro et al. | |
| 7,025,869 B2* | 4/2006 | Fine ...................... | A61K 9/007 128/204.18 |
| 7,114,510 B2* | 10/2006 | Peters .................... | F16K 31/60 137/1 |
| 7,298,280 B2 | 11/2007 | Voege et al. | |
| 7,455,062 B2 | 11/2008 | Roehl et al. | |
| D585,540 S | 1/2009 | Lithgow et al. | |
| 7,523,752 B2 | 4/2009 | Montgomery et al. | |
| D606,655 S | 12/2009 | Wilkinson et al. | |
| 7,681,572 B2 | 3/2010 | Fishman | |
| D613,411 S | 4/2010 | Collins et al. | |
| D619,700 S | 7/2010 | Kenyon et al. | |
| 7,849,854 B2 | 12/2010 | DeVries et al. | |
| D635,244 S | 3/2011 | Virr et al. | |
| 7,927,313 B2 | 4/2011 | Stewart et al. | |
| 7,980,245 B2 | 7/2011 | Rice et al. | |
| D666,299 S | 8/2012 | Bergman et al. | |
| D666,724 S | 9/2012 | Wilhelm | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| D679,800 S | 4/2013 | Gusky et al. | |
| D681,231 S | 4/2013 | Steinhauer et al. | |
| 8,431,163 B2 | 4/2013 | Baldassarre et al. | |
| D693,468 S | 11/2013 | Meng et al. | |
| 8,573,209 B2 | 11/2013 | Bathe et al. | |
| 8,573,210 B2 | 11/2013 | Bathe et al. | |
| D701,963 S | 4/2014 | Abarbanel et al. | |
| 8,776,794 B2 | 7/2014 | Bathe et al. | |
| 8,776,795 B2 | 7/2014 | Bathe et al. | |
| 8,795,741 B2 | 8/2014 | Baldassarre | |
| 8,846,112 B2 | 9/2014 | Baldassarre | |
| 2002/0013551 A1 | 1/2002 | Zaitsu et al. | |
| 2002/0044059 A1 | 4/2002 | Reeder et al. | |
| 2003/0073952 A1* | 4/2003 | Flaherty ............ | A61M 5/14248 604/151 |
| 2003/0145854 A1* | 8/2003 | Hickle .............. | A61M 16/0084 128/204.18 |
| 2005/0139651 A1* | 6/2005 | Lim ........................ | A61M 5/14 235/380 |
| 2005/0172966 A1 | 8/2005 | Blaise et al. | |
| 2006/0264778 A1 | 11/2006 | Lim et al. | |
| 2008/0150739 A1 | 6/2008 | Gamard | |
| 2009/0118594 A1 | 1/2009 | Zdeblick | |
| 2009/0044804 A1 | 2/2009 | Fishman | |
| 2009/0071481 A1 | 3/2009 | Fishman | |
| 2009/0266358 A1 | 10/2009 | Rock et al. | |
| 2011/0048149 A1 | 3/2011 | Nishimura et al. | |

(56) References Cited

U.S. PATENT DOCUMENTS

| | | |
|---|---|---|
| 2011/0240019 A1 | 10/2011 | Fine et al. |
| 2011/0284777 A1 | 11/2011 | Pitchford et al. |
| 2012/0029376 A1 | 2/2012 | Meng et al. |

OTHER PUBLICATIONS

First Action Interview Pilot Program Pre-Interview Communication in U.S. Appl. No. 13/677,483, dated Mar. 20, 2013.
Non-Final Office Action in U.S. Appl. No. 13/509,873, dated Mar. 15, 2013.
Non-Final Office Action in U.S. Appl. No. 14/629,742, dated Jun. 15, 2015.
Non-Final Office Action in U.S. Appl. No. 14/328,150, dated Sep. 24, 2015.
First Action Interview Pilot Program Pre-Interview communication in U.S. Appl. No. 13/493,493, dated Aug. 21, 2012.
Guidance Document for Premarket Notification Submissions for Nitric Oxide Delivery Apparatus, Nitric Oxide Analyzer and Nitrogen Dioxide Analyzer, U.S. Department of Health and Human Services, Food and Drug Administration, Center for Devices and Radiological Health Jan. 24, 2000.
INOMax DS (Delivery System); Operation Manual (800 ppm INOMAX (nitric oxide) for inhalation), Ikaria, Inc., 2010.
INOMAX Label, Center for Drug Evaluation and Research, Application No. NDA 20845, available at http://accessdata.fda.gov/ drugsatfda docs/nda/99/20845 inomax printlbl.pdf, accessed Aug. 9, 2000.
INOvent Delivery System; Operation and Maintenance Manual (CGA Variant), Datex-Ohmeda, Inc., 2000.
International Standard ISO/IEEE 11073-30300—Health Informatics— Point-of-Care Medical Device Communication Part: 20200: Transport Profile—Infrared Wireless, ISO/IEEE 11073-30300:2004(E), First Edition Dec. 15, 2004.
Patent Certification Notice pursuant to Section 505(j)(2)(B)(ii) for U.S. Pat. Nos. 8,282,966; 8,293,284; 8,431,163; 8,795,741; 8,846,112; 8,291,904; 8,573,210; 8,573,209; 8,776,794; and 8,776,795 Nitric Oxide for Inhalation 100 ppm, 800 ppm Praxair Dist, Jan. 6, 2015.
*Praxair Distribution, Inc.* v. *INO Therapeutics, LLC d/b/a Ikaria, Inc.*, Petition for Inter Partes Review of U.S. Pat. No. 8,291,904, dated Mar. 16, 2015.
*Praxair Distribution, Inc.* v. *INO Therapeutics, LLC d/b/a Ikaria, Inc.*, Petition for Inter Partes Review of U.S. Pat. No. 8,573,209, dated Mar. 16, 2015.
*Praxair Distribution, Inc.* v. *INO Therapeutics, LLC d/b/a Ikaria, Inc.*, Petition for Inter Partes Review of U.S. Pat. No. 8,573,210, dated Mar. 16, 2015.
*Praxair Distribution, Inc.* v. *INO Therapeutics, LLC d/b/a Ikaria, Inc.*, Petition for Inter Partes Review of U.S. Pat. No. 8,776,794, dated Mar. 16, 2015.
*Praxair Distribution, Inc.* v. *INO Therapeutics, LLC d/b/a Ikaria, Inc.*, Petition for Inter Partes Review of U.S. Pat. No. 8,776,795, dated Mar. 16, 2015.
Station Opti KINOX Brochure, Air Liguide Sante France 2009.
Using the INOpulse DS Subject Guide, Ikaria, Inc. 2012.
INOmax Label, Nitric Oxide Gas, INO Therapeutics 2013.
INOmax DSIR (Delivery System); Operation Manual (800 ppm INOMAX (nitric oxide) for inhalation, Ikaria, Inc. 2012.
*Praxair Distribution, Inc.* v. *INO Therapeutics, LLC d/b/a Ikaria, Inc.*, Decision to Institute Inter Partes Review of U.S. Pat. No. 8,291,904, dated Sep. 22, 2015.
*Praxair Distribution, Inc.* v. *INO Therapeutics, LLC d/b/a Ikaria, Inc.*, Decision to Institute Inter Partes Review of U.S. Pat. No. 8,573,209, dated Sep. 22, 2015.
*Praxair Distribution, Inc.* v. *INO Therapeutics, LLC d/b/a Ikaria, Inc.*, Decision to Institute Inter Partes Review of U.S. Pat. No. 8,573,210, dated Sep. 22, 2015.

*Praxair Distribution, Inc.* v. *INO Therapeutics, LLC d/b/a Ikaria, Inc.*, Decision to Institute Inter Partes Review of U.S. Pat. No. 8,776,794, dated Sep. 22, 2015.
*Praxair Distribution, Inc.* v. *INO Therapeutics, LLC d/b/a Ikaria, Inc.*, Decision to Institute Inter Partes Review of U.S. Pat. No. 8,776,795, dated Sep. 22, 2015.
Bedfont Scientific Introduces State of the Art Intelligent INO Delivery & Monitoring System, BIOSPACE, http://biospace.comNews/ bedfont-scientific-introducesstate-of-the-art/272542,accessed from the Internet Dec. 8, 2015, Sep. 10, 2012, 10:56 AM, 1 page.
21 C.F.R. Section 807.92—Content and Format of 510(k) Summary, WestlawNext 2015.
21 C.F.R. Section 814.82—Postapproval Requirements, WestlawNext 2015.
Medical Device Classification Product Codes—Guidance for Industry and Food and Drug Administration Staff, U.S. Food & Drug Admin., http://www.fda.gov/RegulatoryInformation/Guidances/ ucm285317.htm, accessed from the Internet Dec. 8, 2015.
FDA Maude Database Example Results for Produce Code MRN (Nitric Oxide Administration Apparatus) between Oct. 1, 2009 and Nov. 30, 2011, by WP Heim, https://www.accessdata.fda.gov/scripts/ cdrh/cfdocs/cfmauderesults.cfm, Nov. 21, 2015.
The New 510(k) Paradigm—Alternative Approaches to Demonstrating Substantial Equivalence in Premarket Notifications, Final Guidance, Food & Drug Admin., http"//www.fda.gov/MedicalDevices/ DeviceRegulationandGuidance/GuidanceDocuments/ucm080187. htm, Mar. 20, 1998.
The 510(k) Program: Evaluation Substantial Equivalence in Premarket Notifications [510(k)], Guidance for Industry and Food and Drug Administration Staff, U.S. Food & Drug Admin., http://www.fda. gov/downloads/MedicalDevices/ . . . /UMC28444.3pdf, issued Jul. 28, 2014.
Bedfont NOxBox & NOxMixer—Technical Guide: issue 6.0 (Software V.17.1), Bedfont Scientific, Ltd., http://www.bedfont,com/file/ php?f=ZmIsZSMjMTM3NA==Sep. 2015.
CareFusion PrinterNOx Operating Manual, CareFusion, Feb. 2010.
Curriculum Vitae of Warren P. Heim, Nov. 20, 2015.
Declaration of Warren P. Heim, P.E. *Praxair Distribution, Inc.* v. *INO Therapeutics, LLC d/b/a Ikaria, Inc.*, Case IPR2015-00884, U.S. Pat. No. 8,291,904, dated Dec. 9, 2015.
Declaration of Warren P. Heim, P.E. *Praxair Distribution, Inc.* v. *INO Therapeutics, LLC d/b/a Ikaria, Inc.*, Case IPR2015-00889, U.S. Pat. No. 8,573,209, dated Dec. 9, 2015.
Declaration of Warren P. Heim, P.E. *Praxair Distribution, Inc.* v. *INO Therapeutics, LLC d/b/a Ikaria, Inc.*, Case IPR2015-00891, U.S. Pat. No. 8,573,210, dated Dec. 9, 2015.
Declaration of Warren P. Heim, P.E. *Praxair Distribution, Inc.* v. *INO Therapeutics, LLC d/b/a Ikaria, Inc.*, Case IPR2015-00888, U.S. Pat. No. 8,776,794 B2, dated Dec. 9, 2015.
Declaration of Warren P. Heim, P.E. *Praxair Distribution, Inc.* v. *INO Therapeutics, LLC d/b/a Ikaria, Inc.*, Case IPR2015-00893, U.S. Pat. No. 8,776,795 B2, dated Dec. 9, 2015.
Definition of "Alarm", Dictionary.com 2015.
Deposition Transcript of Robert T. Stone, Dec. 2, 2015.
English Translation of Opti KINOX Brochure, Air Liquide Santé Apr. 2009.
Enlarged Image of Air Liquide Santë Opti KINOX Station, Apr. 2009.
General Controls for Medical Devices, U.S. Food & Drug Admin., http://www.fda.gov/MedicalDevices/DeviceRegulationandGuidance/ Overview/GeneralandSpecificControls/ucm055910.htm, accessed from the Internet Dec. 8, 2015.
INOmeter EB Operation Manual, INO Therapeutics, 2008.
Letter from Praxair Technology, Inc., to Ikaria, Inc., Nov. 25, 2009.
Maxim Integrated iButton Products: 1-Wire Adapters, http://www. maximintegrated.com/en/products/ibutton/products/1wire adapters. cfm, accessed from the Internet Dec. 8, 2015.
Maxim Integrated Memory Products: iButton 64Kb Memory (DS1996), https://www.maximintegrated.com/en/products/digital/memoryproducts/ DS1996,html, accessed from the internet Dec. 8, 2015.
Medical Device Databases, U.S. Food & Drug Admin., http://fda. gov./medicaldevices/deviceregulationsandguidance/databases/default. htm Dec. 4, 2015.

(56) References Cited

OTHER PUBLICATIONS

Patent Owner INO Therapeutics LLC's Response, *Praxair Distribution, Inc.* v. *INO Therapeutics, LLC d/b/a Ikaria, Inc.*, Case IPR2014-00884, U.S. Pat. No. 8,291,904, dated Dec. 9, 2015.
Patent Owner INO Therapeutics LLC's Response, *Praxair Distribution, Inc.* v. *INO Therapeutics, LLC d/b/a Ikaria, Inc.*, Case IPR2015-00889, U.S. Pat. No. 8,573,209, dated Dec. 9, 2015.
Patent Owner INO Therapeutics LLC's Response, *Praxair Distribution, Inc.* v. *INO Therapeutics, LLC d/b/a Ikaria, Inc.*, Case IPR2015-00891, U.S. Pat. No. 8,573,210, dated Dec. 9, 2015.
Patent Owner INO Therapeutics LLC's Response, *Praxair Distribution, Inc.* v. *INO Therapeutics, LLC d/b/a Ikaria, Inc.*, Case IPR2015-00888, U.S. Pat. No. 8,776,794 B2, dated Dec. 9, 2015.
Patent Owner INO Therapeutics LLC's Response, *Praxair Distribution, Inc.* v. *INO Therapeutics, LLC d/b/a Ikaria, Inc.*, Case IPR2015-00893, U.S. Pat. No. 8,776,795 B2, dated Dec. 9, 2015.
Photographs of Praxair NOMIX Delivery System, 2009.
Praxair NOmix Brochure [Certified English Translation], Praxair, 2009.
Premarket Notification 510(k), U.S. Food & Drug Admin., http://www.fda.gov/MedicalDevices/DeviceRegulationandGuidance/HowtoMarketYourDevice/PremarketSubmissions/PremarketNotification510k/, accessed from the Internet Dec. 8, 2015.
Regulatory Controls, U.S. Food & Drug Admin., http://www.fda.gov/MedicalDevices/DeviceRegulationandGuidance/Overview/GeneralandSpecialControls/ucm2005378.htm, accessed from the Internet Dec. 8, 2015.
Non-Final Office Action in U.S. Appl. No. 14/065,962, dated Jun. 23, 2015.
21 C.F.R. Section 814.20—Application, WestlawNext 2015.

\* cited by examiner

GAS DELIVERY DEVICE AND SYSTEM

CROSS-REFERENCE TO RELATED APPLICATIONS

This application is a continuation of U.S. Pat. No. 9,265,911 filed on Oct. 29, 2013, which is a continuation of U.S. Pat. No. 8,573,209 filed on May 15, 2012, which is the National Phase entry of PCT/US2011/02319, filed Jan. 6, 2011, the entire content of which are incorporated herein by reference in their entirety.

TECHNICAL FIELD

Embodiments of the present invention relate to gas delivery device for use in a gas delivery system for administering therapy gas and methods of administering therapy gas.

BACKGROUND

Certain medical treatments include the use of gases that are inhaled by the patient. Gas delivery devices are often utilized by hospitals to deliver the necessary gas to patients in need. It is important when administering gas therapy to these patients to verify the correct type of gas and the correct concentration are being used. It is also important to verify dosage information and administration.

Known gas delivery devices may include a computerized system for tracking patient information, including information regarding the type of gas therapy, concentration of gas to be administered and dosage information for a particular patient. However, these computerized systems often do not communicate with other components of gas delivery devices, for example, the valve that controls the flow of the gas to the computerized system and/or ventilator for administration to the patient. In addition, in known systems, the amount of gas utilized by a single patient is often difficult or impossible to discern, leading to possible overbilling for usage.

There is a need for a gas delivery device that integrates a computerized system to ensure that patient information contained within the computerized system matches the gas that is to be delivered by the gas delivery device. There is also a need for such an integrated device that does not rely on repeated manual set-ups or connections and which can also track individual patient usage accurately and simply.

SUMMARY

Aspects of the present invention pertain to a gas delivery device that may be utilized with a gas delivery system and methods for administering therapy gas to a patient. One or more embodiments of the gas delivery devices described herein may include a valve and a circuit with a valve memory in communication with a valve processor and a valve transceiver. One or more embodiments of the gas delivery systems described herein incorporate the gas delivery devices described herein with a control module including a central processing unit (CPU) in communication with a CPU memory and CPU transceiver. As will be described herein, the valve transceiver and the CPU transceiver may be in communication such that information or data from the valve memory and the CPU memory may be communicated to one another. The information communicated between the valve memory and the CPU memory may be utilized for selecting a therapy for delivery to a patient and controlling delivery of the selected therapy to the patient. The gas delivery devices and systems described herein may be utilized with medical devices such as ventilators and the like to delivery gas to a patient.

A first aspect of the present invention pertains to a gas delivery device. In one or more embodiments, the gas delivery device administers therapy gas from a gas source under the control of a control module. In one variant, the gas delivery device may include a valve attachable to the gas source and a circuit. The valve may include an inlet and an outlet in fluid communication and a valve actuator to open and close the valve to allow the gas to flow through the valve to a control module. The circuit of one or more embodiments includes a memory, a processor and a transceiver in communication with the memory to send wireless optical line-of-sight signals to communicate information stored or retained within the memory to the control module that controls gas delivery to a subject. In one or more alternative embodiments, the signals to communicate information stored or retained within the memory to the control module that controls gas delivery to a subject may be communicated via a wire. Examples of such wired signals may incorporate or utilize an optical cable, wired pair and/or coaxial cable. The circuit may include a memory to store gas data, which may include one or more of gas identification, gas expiration date and gas concentration. The transceiver may communicate to send the gas data to the control module via wireless optical line-of-sight signals.

In one or more embodiments, the valve may include a data input in communication with said memory, to permit a user to enter the gas data into the memory. The gas data may be provided in a bar code that may be disposed on the gas source. In such embodiments, the gas data may be entered into the data input of the valve for storage in the memory by a user-operated scanning device in communication with the data input. Specifically, the user may scan the bar code to communicate the gas data stored therein to the valve memory via the data input.

In one or more embodiments, the valve may include a power source. In such embodiments, the power source may include a battery or other portable power source. In one or more embodiments, the valve transceiver may periodically send the wireless optical line-of-sight signals to the control module, wherein the signals are interrupted by a duration of time at which no signal is sent. In one or more specific embodiments, the duration of time at which no signal is sent comprises about 10 seconds.

A second aspect of the present invention pertains to a gas delivery device, as described herein, and a control module in fluid communication with the outlet of the valve of the gas delivery device and with a gas delivery mechanism, such as a ventilator. In one or more embodiments, the control module may include a CPU transceiver to receive line-of-sight signals from the transceiver and a CPU in communication with the CPU transceiver. The CPU carries out the instructions of a computer program or algorithm. As used herein the phrase "wireless optical line-of-sight signal" includes infrared signal and other signals that require a transmitter and receiver or two transceivers to be in aligned such that the signal may be transmitted in a straight line. The CPU may include a CPU memory that stores the gas data that is communicated by the valve transceiver of the gas delivery device to the CPU transceiver.

In one or more embodiments, the gas delivery system may incorporate a valve with a timer including a calendar timer and an event timer for determining or marking the date and time that the valve is opened and closed and the duration of time the valve is opened. In such embodiments, the valve memory stores the date and time of opening and closing of the valve and the duration of time that the valve is open and the valve transceiver communicates the date and time of opening and closing of the valve to the CPU transceiver for storage in the CPU memory.

In one or more variants, the gas delivery system may incorporate a control module that further includes an input means to enter patient information into the CPU memory. The control module may also have a real time clock built into the CPU module such that the control module knows what the current time and date is and can compare that to the expiration date stored in the gas delivery device. If the expiration date is passed the current date then the control module can cause an alarm and not deliver drug to the patient. When the term "patient information" is used, it is meant to include both patient information entered by the user and information that is set during manufacturing, such as the gas identification and the gas concentration that the control module is setup to deliver. The control module may also include a display. In one or more embodiments, the display incorporates an input means for entering patient information into the CPU memory. In one or more embodiments, the CPU of the control module compares the patient information entered into the CPU memory via the input means and the gas data from the transceiver. The CPU or control module may include comprises an alarm that is triggered when the patient information entered into the CPU memory and the gas data from the transceiver do not match or conflict. As used herein the phrase "do not match," includes the phrase "are not identical," "are not substantially identical," "do conflict" and/or "do substantially conflict." The CPU determines whether the patient information and additional data, or other data set matches by performing a matching algorithm which includes criteria for establishing whether one set of data (i.e. patient information) and another set of data match. The algorithm may be configured to determine a match where every parameter of the data sets match or selected parameters of the data sets match. The algorithm may be configured to include a margin of error. For example, where the patient information require a gas concentration of 800 ppm, and the additional data includes a gas concentration of 805 ppm, the algorithm may be configured to include a margin of error of ±5 ppm such it determines that the patient information and the additional data match. It will be understood that determining whether the patient information and additional data match will vary depending on the circumstances, such as variables in measuring gas concentration due to temperature and pressure considerations.

A third aspect of the present invention pertains to a control module memory comprising instructions that cause a control module processor to receive gas data from a valve via a wireless optical line-of-sight signal. The valve may be connected to a gas source and may include a memory for storing the gas data. The control module memory may include instructions that cause the control module processor to compare the gas data with user-inputted patient information. The user-inputted patient information may be stored within the control module memory. Gas data may be selected from one or more of gas identification, gas expiration date and gas concentration. In one or more embodiments, the control module memory may include instructions to cause the control module processor to coordinate delivery of therapy to the patient with a medical device, such as a ventilator and the like for delivering gas to a patient, via the wireless optical line-of-sight signal. The control module memory may also include instructions to cause the control module processor to select a therapy for delivery to a patient based on the received patient information and control delivery of the selected therapy to the patient.

In one or more embodiments, the memory may include instructions to cause the processor to detect the presence of more than one valve and whether more than one valve is open at the same time. In accordance with one or more specific embodiments, the memory includes instructions to cause the processor to receive a first valve status selected from a first open position and a first closed position from a first valve via a first wireless optical line-of-sight signal with the first valve connected to a first gas source, receive a second valve status selected from a second open position and a second closed position from a second valve via a second wireless optical line-of-sight signal with the second valve connected to a second gas source, compare the first valve status and the second valve status, and emit an alarm if the first valve status comprises the first open position and the second valve status comprises the second open position. In one or more alternative embodiments, the first valve status and the second valve status may be communicated to the processor via a single wireless optical line-of-sight signal, instead of separate wireless optical line-of-sight signals. In a more specific embodiment, the memory of one or more embodiments may include instructions to cause the processor to terminate delivery of therapy if the first valve status comprises the first open position and the second valve status comprises the second open position.

In one or more embodiments, the memory may include instructions to cause the processor to emit an alarm when a desired dose has been delivered through a valve. In such embodiments, the processor may include a memory to store the desired dose or dosage information. In such embodiments, the memory may include instructions to cause the processor to receive gas delivery information or information regarding the amount of gas delivered and compare the gas delivery information to the dosage information and emit an alarm when the gas delivery information and the dosage information match. As used herein, the term "dosage information" may be expressed in units of parts per million (ppm), milligrams of the drug per kilograms of the patient (mg/kg), millimeters per breath, and other units known for measuring and administering a dose. In one or more embodiments, the dosage information may include various dosage regimes which may include administering a standard or constant concentration of gas to the patient, administering a gas using a pulsed method. Such pulsing methods includes a method of administering a therapy gas to a patient during an inspiratory cycle of the patient, where the gas is administered over a single breath or over a plurality of breaths and is delivery independent of the respiratory pattern of the patient.

A fourth aspect of the present invention pertains to a method for administering a therapy gas to a patient. In one or more embodiments, the method includes establishing communication between the patient and a gas delivery device via a transceiver, wherein the gas delivery device comprises a first memory including gas data, comparing the gas data with patient information stored within a second memory. The second memory may be included within a control module in communication with the gas delivery device. After comparing the gas data and the patient information, the method may further include coordinating delivery of therapy to a patient with the gas delivery device via a wireless optical line-of-sight signal, selecting a therapy for delivery to the patient based on the comparison of the gas data and the patient information and controlling delivery of the selected therapy to the patient. In one or more specific embodiments, the method may include entering the gas data into the first memory of the gas delivery device and/or entering the patient information into the second memory. In embodiments in which the method includes entering the patient information into the second memory, the control module may include input means by which patient information may be entered into the second memory. In one or more variants, the method includes ceasing delivery of the selected therapy to the patient based on the comparison of the gas data and the patient information. The method may include emitting an alert based on the comparison of the gas data and the patient information.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Figure 1:
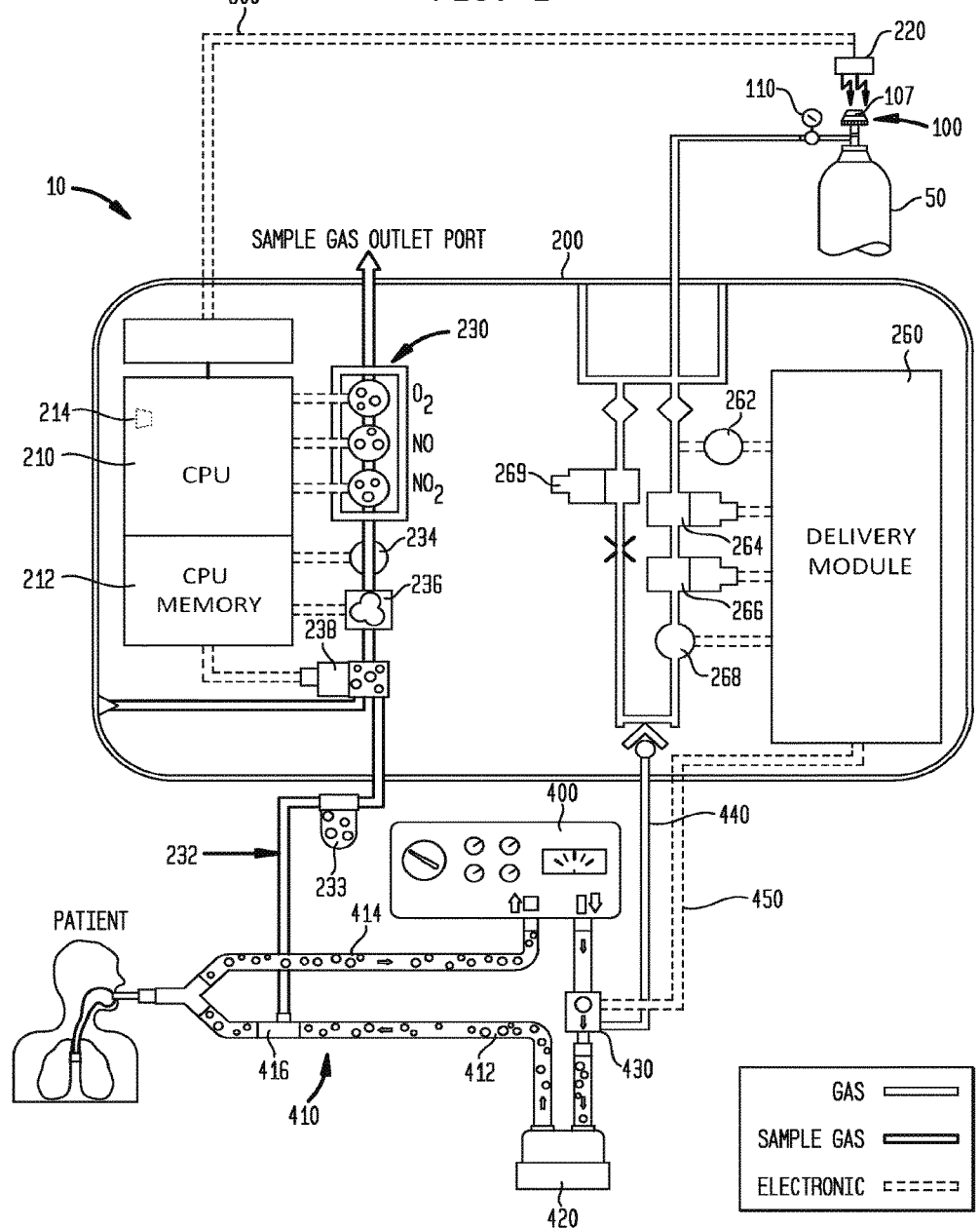
FIG. 1 is a diagram of a gas delivery system including a gas delivery device, a gas source, a control module and a gas delivery mechanism, according to one or more embodiments.

A system for the administration of therapy gas is described. A first aspect of the present invention pertains to a gas delivery device. The gas delivery device may include a valve assembly including at least one valve with a circuit. The gas delivery system may include the gas delivery device (e.g. valve assembly, including a valve and a circuit) in communication with a control module to control the delivery of gas from a gas source to a ventilator or other device used to introduce the gas into the patient, for example, a nasal cannula, endotracheal tube, face mask or the like. Gas source, as used herein, may include a gas source, gas tank or other pressured vessel used to store gases at above atmospheric pressure. The gas delivery system 10 is shown in FIG. 1. In FIG. 1, the valve assembly 100, including a valve 107 or valve actuator and a circuit 150, is in communication with a control module 200 via a wireless line-of-sight connection 300. In one or more alternative embodiments, communication between the valve assembly 100 and the control module 200 may be established via a wired signal. The gas delivery system 10 also includes a gas source 50 including a gas attached to the valve assembly 100 and a gas delivery mechanism, which includes a ventilator 400 and a breathing circuit 410, in communication with the control module 200.

Figure 2:
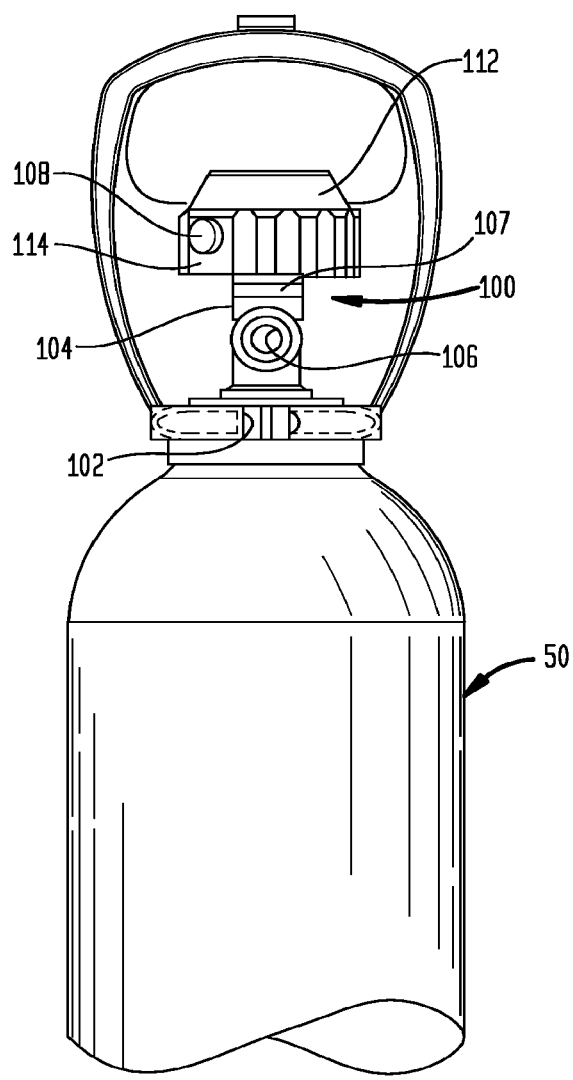
FIG. 2 illustrates a valve assembly of the gas delivery device according to one or more embodiments attached to a gas source.
Figure 3:
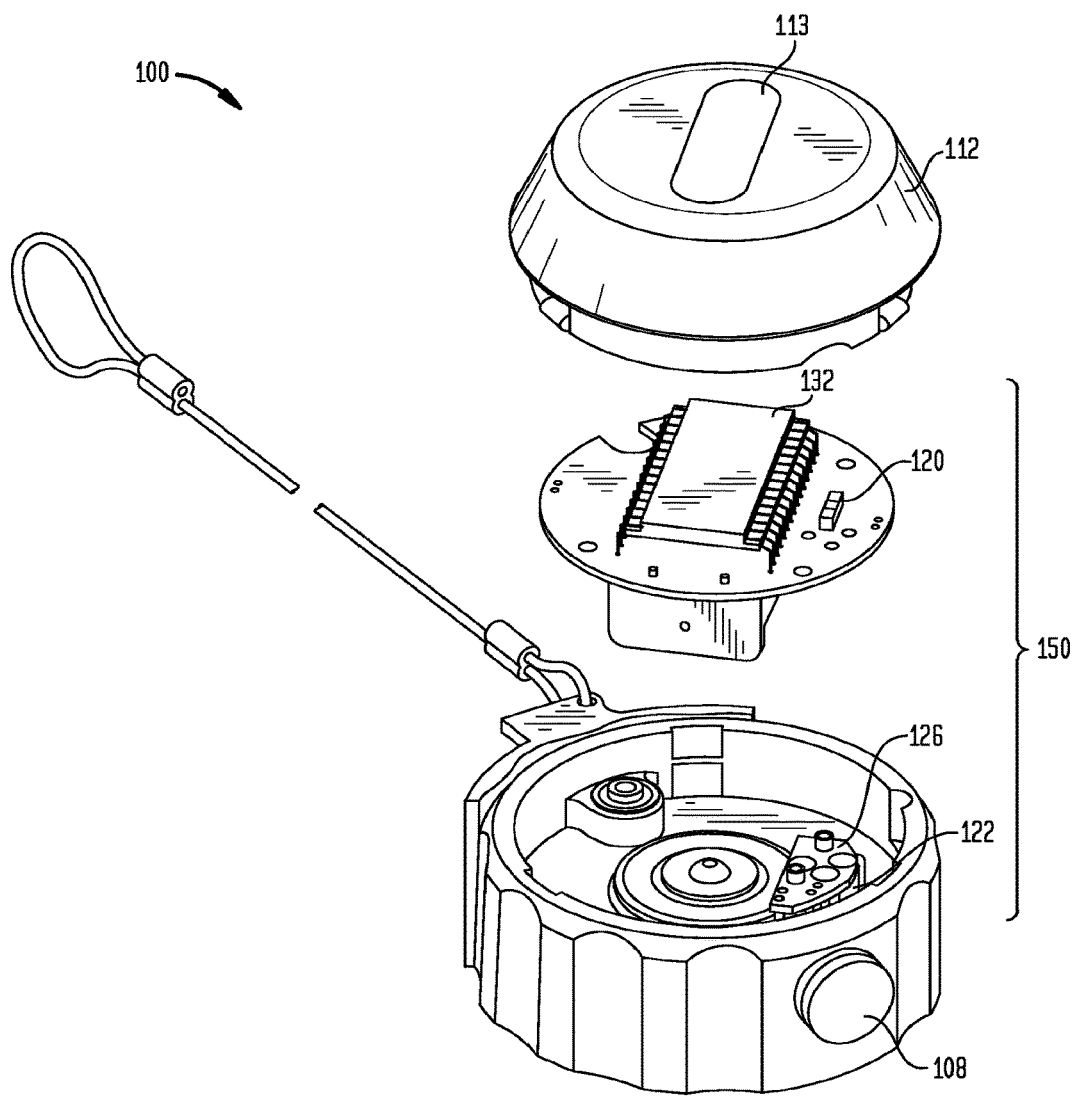
FIG. 3 illustrates a disassembled view of the valve assembly shown in FIG. 2.
Figure 4:
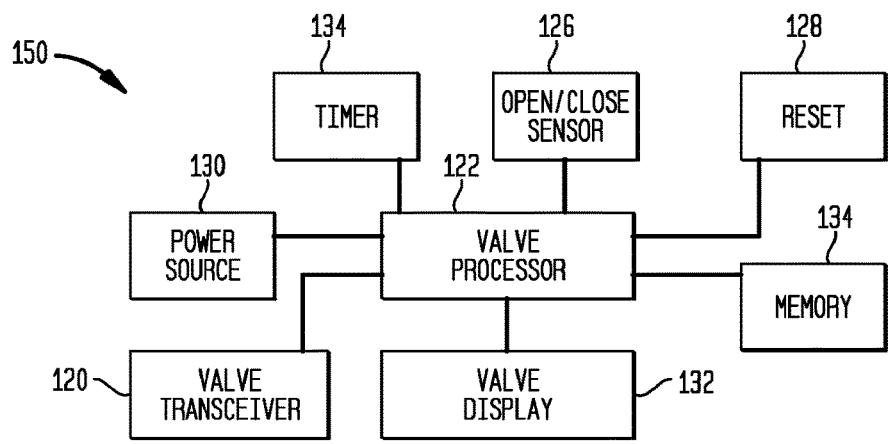
FIG. 4 is a diagram showing a circuit supported in the valve assembly shown in FIG. 2, according to one or more embodiments.

FIGS. 2-4 illustrate the components of the valve assembly 100. The valve assembly 100 includes a valve 107 and a circuit 150 supported in the valve assembly. FIG. 3 illustrates a disassembled view of the valve assembly 100, showing components of the physical circuit 150 and the valve 107. As shown in FIG. 4, which will be described in more detail below, the circuit 150 of the gas delivery device includes a valve transceiver 120 for establishing communication with the control module 200, which will also be discussed in greater detail below.

Referring to FIG. 2, the valve 107 includes an attachment portion 102 for attaching the valve assembly 100 to the gas source 50, an inlet 104 and an outlet 106 in fluid communication with the inlet 104, as more clearly shown in FIG. 2.

FIG. 3 illustrates a disassembled view of the valve assembly 100 and illustrates an actuator 114 is disposed on the valve 107 and is rotatable around the valve 107 for opening and closing the valve 107. The actuator 114 includes a cap 112 mounted thereto. As shown in FIG. 3, the circuit 150 may include a data input 108 disposed on the actuator 114. The data input 108 may be disposed at other locations on the valve 107. In one or more variants, the data input may include a port such as a USB port, a receiver for receiving electronic signals from a transmitted or other known input means known in the art for entering information or data into a memory.

FIG. 4 illustrates a block diagram of the circuit 150. The circuit 150 shown in FIG. 4 includes a valve processor 122, a valve memory 134, a reset 128, a valve transceiver 120 and a power source 130. The circuit 150 may also include support circuits a timer 124, a sensor 126 and/or other sensors. Referring to FIG. 3, the circuit 150 is supported within the valve assembly 100, with the physical components of the circuit 150 specifically disposed between actuator 114 and the cap 112. As shown in FIG. 3, the valve display 132 and the valve transceiver 120 are disposed adjacent to the cap 112, such that the valve display 132 is visible through a window 113. The sensor 126 and the valve processor 122 are disposed beneath the valve display 132 and the valve transceiver 120, within the actuator 114.

The valve processor 122 may be one of any form of computer processor that can be used in an industrial setting for controlling various actions and sub-processors. The valve memory 134, or computer-readable medium, may be one or more of readily available memory such as electrically erasable programmable read only memory (EEPROM), random access memory (RAM), read only memory (ROM), floppy disk, hard disk, or any other form of digital storage, local or remote, and is typically coupled to the valve processor 122. The support circuits may be coupled to the valve processor 122 for supporting the circuit 150 in a conventional manner. These circuits include cache, power supplies, clock circuits, input/output circuitry, subsystems, and the like.

Figure 5:
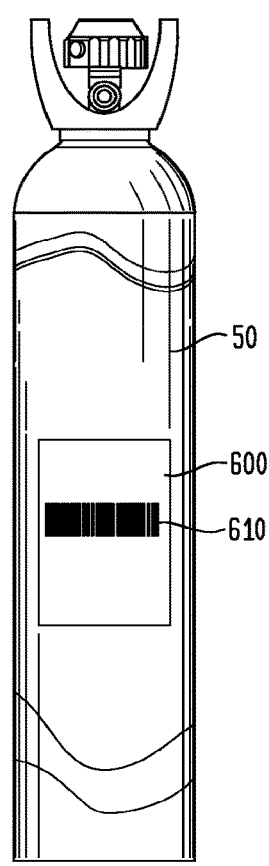
FIG. 5 illustrates an exemplary gas source for use with the valve assembly shown in FIG. 2.

In the embodiment shown, the valve memory 134 communicates with a data input 108 disposed on the side of the actuator 114. The data input 108 shown in FIGS. 3-4 is used to transfer data from the valve memory 134 to other devices or to input data into the valve memory 134. For example, gas data, which includes information regarding the gas contained within the gas source, may be entered into the valve memory 134 via the data input 108. In one or more alternative embodiments, the gas data may be programmed or directly entered into the valve memory 134 by the gas supplier. In one or more embodiments, the gas data may be provided in the form of a bar code 610 that is disposed on a label 600 that is affixed on a to the side of the gas source, as shown in FIG. 5. The bar code 610 may be disposed directly on the gas source. An external scanning device in communication with the electronic data input 108 may be provided and may be used to scan the bar code 610 and convey the information from the bar code 610 to the valve memory 134. Gas data may include information regarding the gas composition (e.g., NO, $O_2$, $NO_2$, CO, etc.), concentration, expiration date, batch and lot number, date of manufacturing and other information. Gas data may be configured to include one or more types of information. The valve processor 122 may include instructions to convey all or a pre-determined portion of the gas data via the valve transceiver 120 to another transceiver.

In embodiments that utilize a timer 124, the timer 124 may include two sub-timers, one of which is a calendar timer and the other of which is an event timer. The reset 128 may be located inside the actuator 114 and may be depressed to reset the event timer. The cap 112 also includes a window 113 that allows the user to see the valve display 132 disposed within the cap 112 that displays information regarding whether the actuator 114 is opened or closed and the duration the valve 107 was opened or closed. In one or more embodiments, the valve display 132 may alternate flashing of two different numbers, a first number may be accumulated open time, and the second number may be the time at which the valve 107 was opened for the current event. The time at which the valve 107 was opened for a current event may be preceded by other indicators.

The sensor 126 disposed within the actuator 114 may include a proximity switch model MK20-B-100-W manufactured by Meder Inc. The sensor 126 utilized in one or more embodiments may cooperate with a magnet (not shown) to sense whether the actuator 114 is turned on or turned off. Such sensors are described in U.S. Pat. No. 7,114,510, which is incorporated by reference in its entirety.

For example, the sensor 126 and a corresponding magnet (not shown) may be disposed on a stationary portion of the valve 107. When the actuator 114 is rotated to the closed position, the sensor 126 is adjacent to the magnet that is in a fixed position on the valve 107. When the sensor 126 is adjacent to the magnet, it sends no signal to the valve processor 122, thereby indicating that the actuator 114 is in the "closed" position or has a valve status that includes an open position or a closed position. When the actuator 114 is rotated to open the valve 107, the sensor 126 senses that it has been moved away from the magnet and sends a signal to the valve processor 122, indicating an "open" position. The valve processor 122 instructs the valve memory 134 to record the event of opening the valve 107 and to record the time and date of the event as indicated by the calendar timer. The valve processor 122 instructs the valve memory 134 to continue checking the position of the valve 107 as long as the valve 107 is open. When the valve 107 is closed, the valve processor 122 uses the logged open and close times to calculate the amount of time the valve 107 was open and instructs the valve memory 134 to record that duration and the accumulated open time duration. Thus, every time the valve 107 is opened, the time and date of the event is recorded, the closing time and date is recorded, the duration of time during which the valve 107 is open is calculated and recorded, and the accumulated open time is calculated and recorded.

Figure 6:
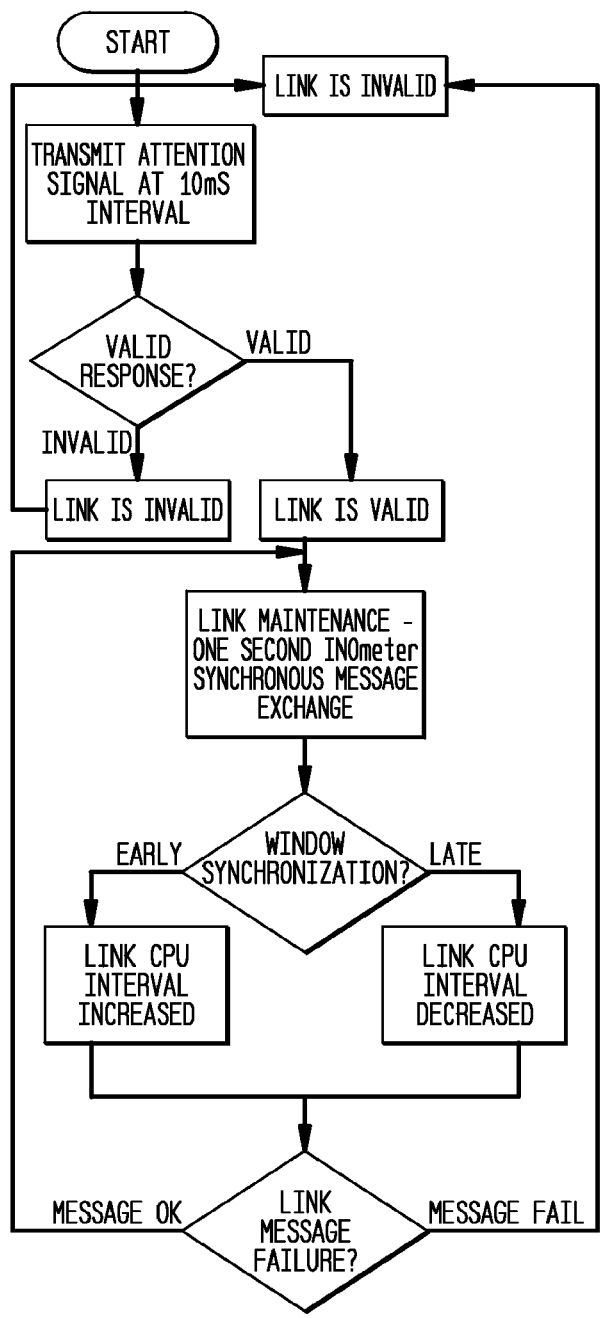
FIG. 6 is an operational flow diagram of the communication between the circuit of the gas delivery device shown in FIG. 1 with a control module regarding the establishment of communication between the circuit and the control module

In one or more embodiments in which the power source 130 includes a battery, the valve transceiver 120 may be configured to communicate with the CPU transceiver 220 to preserve the life of the battery. In this embodiment the valve transceiver 120 is only turned on to receive a signal from the Control Module CPU transceiver 220 for 20 msec every second. The control module CPU transceiver 220 sends out a short transmit signal continuously and if the valve transceiver 120 is present it responds in the 20 msec interval. This conserves battery power as the valve transceiver 120 is only powered on for 20 msec every second. When the valve transceiver 120 responds it includes in its signal information regarding whether the communication from the control module CPU transceiver 220 was early or late within this 20 msec window. This ensures that once communications has been established it is synchronized with the 20 msec window that the valve transceiver 120 is powered on and able to receive communications. For example, as shown in FIG. 6, the valve transceiver 120 sends a wireless optical line-of-sight signal during a pre-determined interval in response to a signal from the control module CPU transceiver 220. The wireless optical line-of-sight signals sent by the valve transceiver 120 are a series of on off cycles where the transmitter is either transmitting light or is not and these correspond to digital binary signals. The mechanism by which the valve transceiver sends a wireless optical line-of-sight signal may be construed as a series of digital on off signals that correspond to data being transmitted. Once communications has been established between the control module CPU transceiver 220 and the valve transceiver 120, the interval between communication signals may be in the range from about 20 seconds to about 5 seconds. In one or more specific embodiments, the interval or duration between transceiver signals may be about 10 seconds.

As will be described in more detail below, the control module 200 includes a CPU 210 which is connected to a CPU transceiver 220 which can send and receive wireless optical line-of-sight signals. The CPU transceiver 220 sends out a signal and waits for a response from the valve transceiver 120 when communication or more specifically, line-of-sight communication is established between the CPU transceiver 220 and the valve transceiver 120. If no response is sent by the valve transceiver 120, the CPU transceiver 220 sends another signal after a period of time. This configuration preserves battery life because the valve transceiver 120 does not continuously send a signal unless requested to by the CPU 210. This is important as the gas delivery device and gas source spends most of its time in shipping and storage prior to being placed on the gas delivery system, if it was transmitting all this time trying to establish communications with the control module it would be consuming the battery life significantly.

The valve processor 122 may include link maintenance instructions to determine whether the interval should be increased or decreased. As shown in FIG. 6, when a valid link is established between the valve transceiver 120 and CPU transceiver 121, the valve processor 122 executes the link maintenance instructions to increase the interval or decrease the interval.

As shown more clearly in FIG. 1, valve assembly 100 and gas source 50 is in communication with a control module 200, which is in communication with a gas delivery mechanism. The gas delivery mechanism shown in FIG. 1 includes a ventilator 400 with associated breathing circuit 410. The control module 200 may include a CPU 210 and a CPU transceiver 220 in communication with the circuit 150 via the valve transceiver 120. The control module 200 also includes a CPU memory 212 in communication with the CPU transceiver 220 to store patient information, information or data received from the valve transceiver 120 and other information. The control module 200 may also include support circuits. The CPU 210 may be one of any form of computer processor that can be used in an industrial setting for controlling various actions and sub-processors. The CPU memory 212, or computer-readable medium, may be one or more of readily available memory such as random access memory (RAM), read only memory (ROM), floppy disk, hard disk, or any other form of digital storage, local or remote, and is typically coupled to the CPU 210. The support circuits may be coupled to the CPU 210 for supporting the control module 200 in a conventional manner. These circuits include cache, power supplies, clock circuits, input/output circuitry, subsystems, and the like. The CPU 210 may also include a speaker 214 for emitting alarms. Alternatively, alarms may also be displayed visually on a display. As shown in FIG. 1, the control module 200 may also include a regulator 110 and, optionally, pressure gauges and flow meters for determining and/or controlling the gas flow from the gas source 50.

In one or more embodiments, the CPU transceiver 220 is disposed on a cover portion 225 (shown more clearly in FIG. 7), that is part of a cart 500 (show more clearly in FIG. 7) onto which the control module 200 is disposed. The cover portion 225 in one or more embodiments is in communication with the control module 200. Communication between the cover portion 225 and the control module 200 may be established wirelessly or via a cable. As will be discussed in greater detail below, the valve assembly 100, including the valve 107, the circuit 150 and a gas source 50 attached to the valve 107, are placed on the cart 500 in proximity and in a light-of-sight path with the CPU transceiver 220. When properly configured such that communication is established between the valve transceiver 120 and the CPU transceiver 220, the CPU transceiver 220 is positioned directly above the valve transceiver 120, as shown more clearly in FIG. 9. In one or more alternative embodiments, the CPU transceiver 220 may be disposed on the CPU 210.

The CPU 210 may be in communication with a plurality of gas sensors 230 for determining the concentration of a sample of gas drawn via a sample line 232 and a sample line inlet 280 (shown more clearly in FIG. 1) disposed on the control module 200. As will be discussed in greater detail, the sample line 232 draws a sample of gas from a breathing circuit 410 of a ventilator 400 when the ventilator is in fluid communication with the control module 200 and gas is being delivered to the ventilator. The CPU 210 may also be in communication with a sample flow sensor 234 for sensing the flow of the sample drawn via sample line 232, a pump 236 for drawing the sample via the sample line 232 to the flow sensor 234 and zero valve 238 controlling the flow of the sample via the sample line 232 to the sample pump 236, sample flow sensor 234 and the plurality of CPU sensors. The sample line 232 may include a water trap 233 for collecting any water or liquid from the sample.

The control module 200 may also include a delivery module 260 for regulating the flow of gas from the gas source 50 to the ventilator 400. The delivery module 260 may include a pressure switch 262 for determining a gas supply pressure is present, a pressure shut-off valve 264, a proportional valve 266 and a delivery flow sensor 268. The delivery module 260 may also include a backup on/off switch 269. The detailed method of how the delivery module delivers the gas to the ventilator circuit is described in U.S. Pat. No. 5,558,083 which is incorporated here by reference in its entirety.

The ventilator 400 shown in FIG. 1 is in fluid communication with the control module 200 via an injector tubing 440 and in electrical communication via an injector module cable 450. The control module 200 and more specifically, the CPU 210, is in fluid communication with the ventilator 400 via the sample line 232. The ventilator 400 may include a breathing circuit 410 with an inspiratory limb 412 and an expiratory limb 414 in fluid communication with the ventilator 400. The inspiratory limb 412 may be in fluid communication with a humidifier 420, which is in fluid communication with the ventilator 400 via an injector module 430. The inspiratory limb 412 carries gas to the patient and the expiratory limb 414 carries gas exhaled by the patient to the ventilator 400. The injector module 430 shown in FIG. 1 is in fluid communication with the gas source 50 via the injector tubing 440 and in electronic communication with the delivery module 260 via the injector module cable 450 such that the delivery module 260 can detect and regulate the flow of gas from the gas source 50 to the ventilator 400. Specifically, the injector module 430 is in fluid communication with the gas source 50 via an injector tubing 440, which is in fluid communication with one or more of the pressure switch 262, pressure shut-off valve 246, proportional valve 266, flow sensor 268 and the backup switch 269 of the delivery module 260. The injector module 430 may also be in electronic communication with the delivery module 260 via the injector module cable 450. The inspiratory limb 412 of the ventilator 400 may include a sample tee 416 for facilitating fluid communication between the inspiratory limb 412 of the breathing circuit and the sample line 232.

Figure 7:
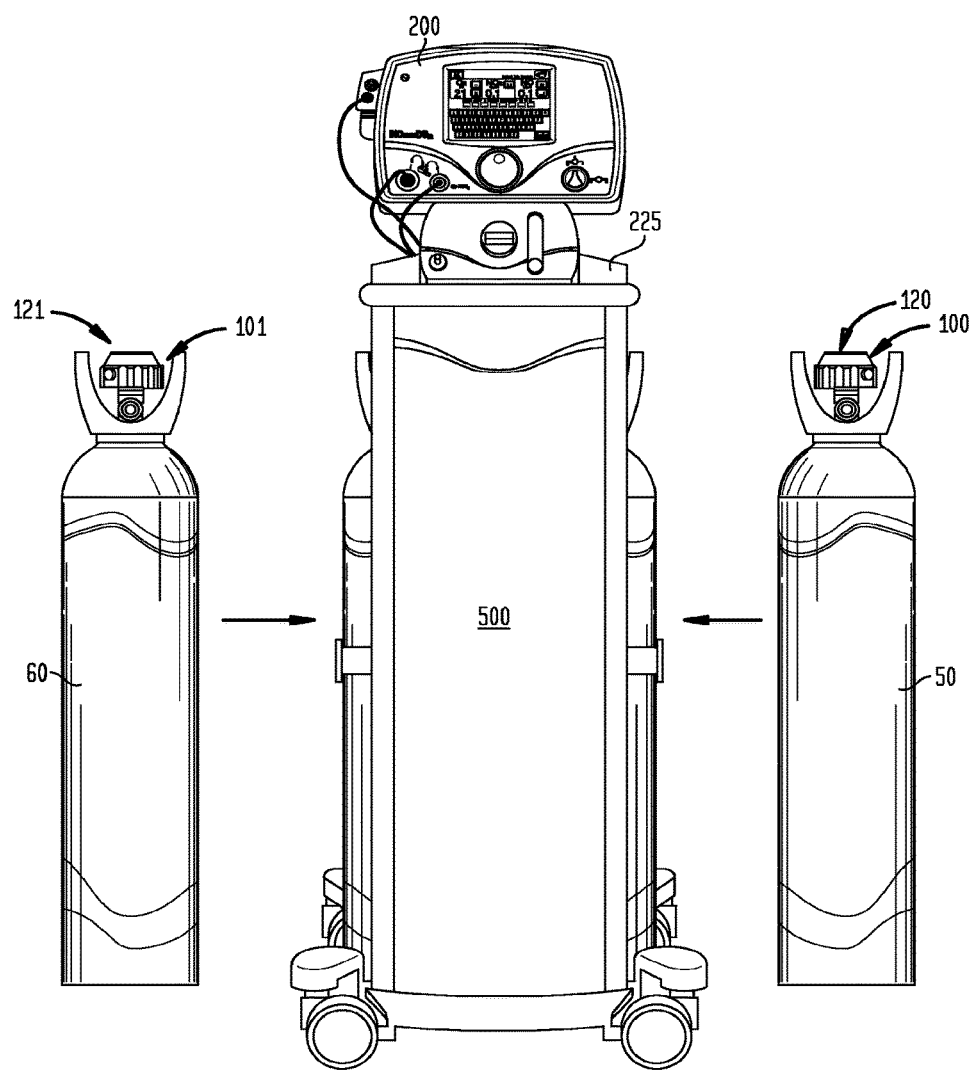
FIG. 7 illustrates a front view of an exemplary gas delivery system.
Figure 8:
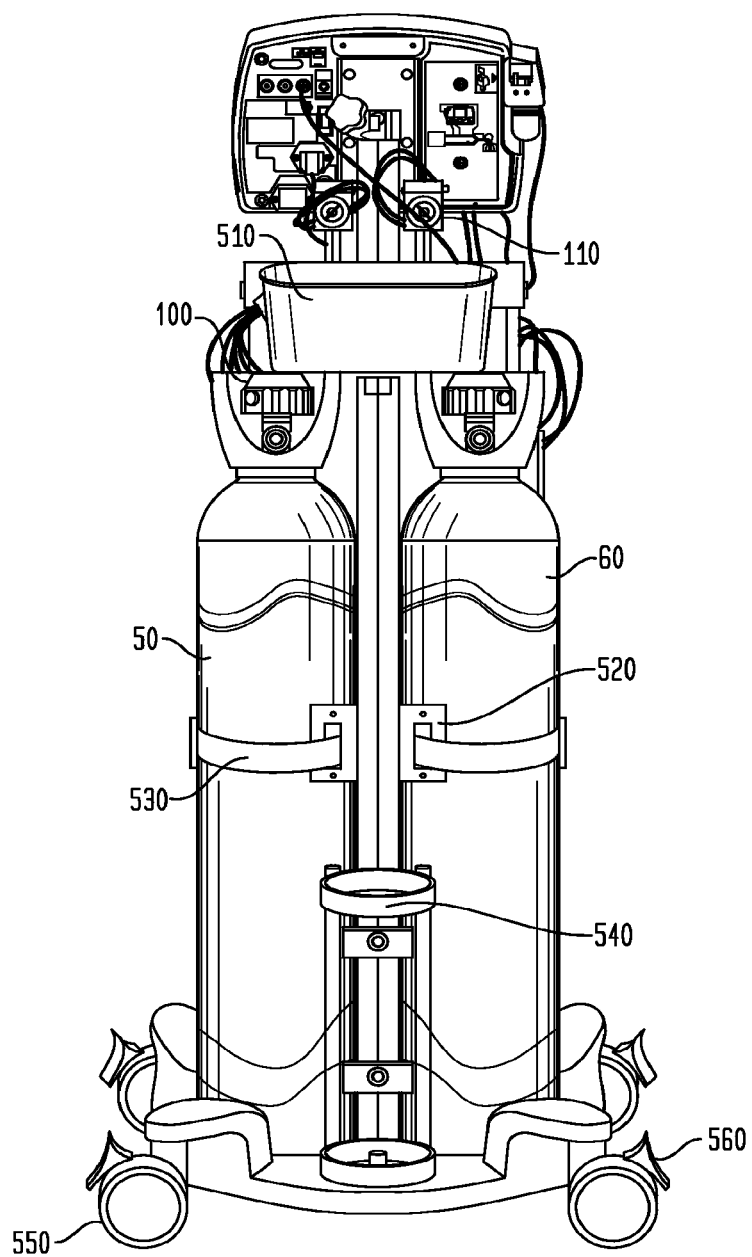
FIG. 8 illustrates a back view of the gas delivery system shown in FIG. 7.
Figure 9:
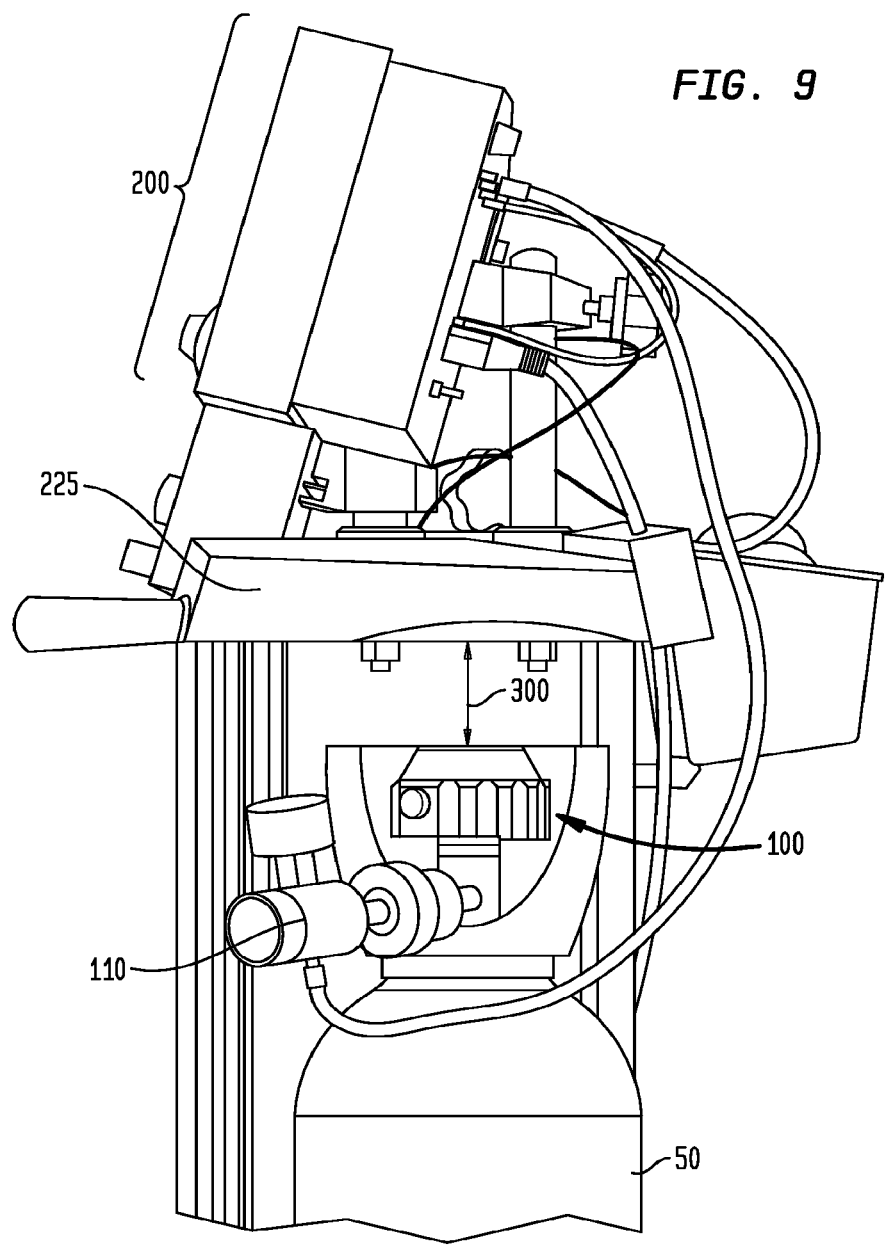
FIG. 9 illustrates a partial side view of the gas delivery system shown in FIG. 7.

As discussed above, the control module 200 may be disposed or attached on a cart 500, as shown in FIGS. 7-9 to facilitate movement of the gas source 50 and the gas delivery device to a patient in need of gas therapy. The gas source 50 and the valve assembly 100 attached thereto may be placed on the cart 500 in proximity to the control module 200. More specifically, as shown in FIG. 7, the gas source 50 is placed on the cart 500 such that the valve transceiver 120 is in proximity of the CPU transceiver 220 and a line-of-sight path is established between the valve transceiver 120 and the CPU transceiver 220. In this configuration, the CPU 210 detects the presence of the circuit 150 and thus the gas source 50 via the CPU transceiver 220.

As shown in FIGS. 7-9, the gas delivery device may include more than one valve, with each valve being attached to a single gas source. In such embodiments which utilize a second gas source 60 with a second valve assembly 101, the second valve assembly 101 is positioned in proximity and in a light-of-sight path with a second CPU transceiver as the gas source 60 is loaded onto the cart. The second CPU transceiver 222 establishes communication with the second valve assembly 101 and thus detects the presence of a second gas source 60. In the embodiment shown in FIGS.

7-9, the second CPU transceiver 222 may also be disposed on the cover portion 225 of a cart. In one or more alternative embodiments, the second CPU transceiver 222 may be disposed on the CPU 210.

As shown in FIG. 8, the cart 500 may include an optional small bin 510, a mount 512 for supporting the control module 200 on the cart 500, at least one a holding bracket 520, at least one mounting strap 530, an auxiliary bracket 540, for holding an auxiliary gas source, a plurality of casters 550 and a caster lock lever 560 disposed on each of the plurality of casters 550. The cart 500 may include a mount 570 for mounting the control module 200 on to the cart.

Figure 10:
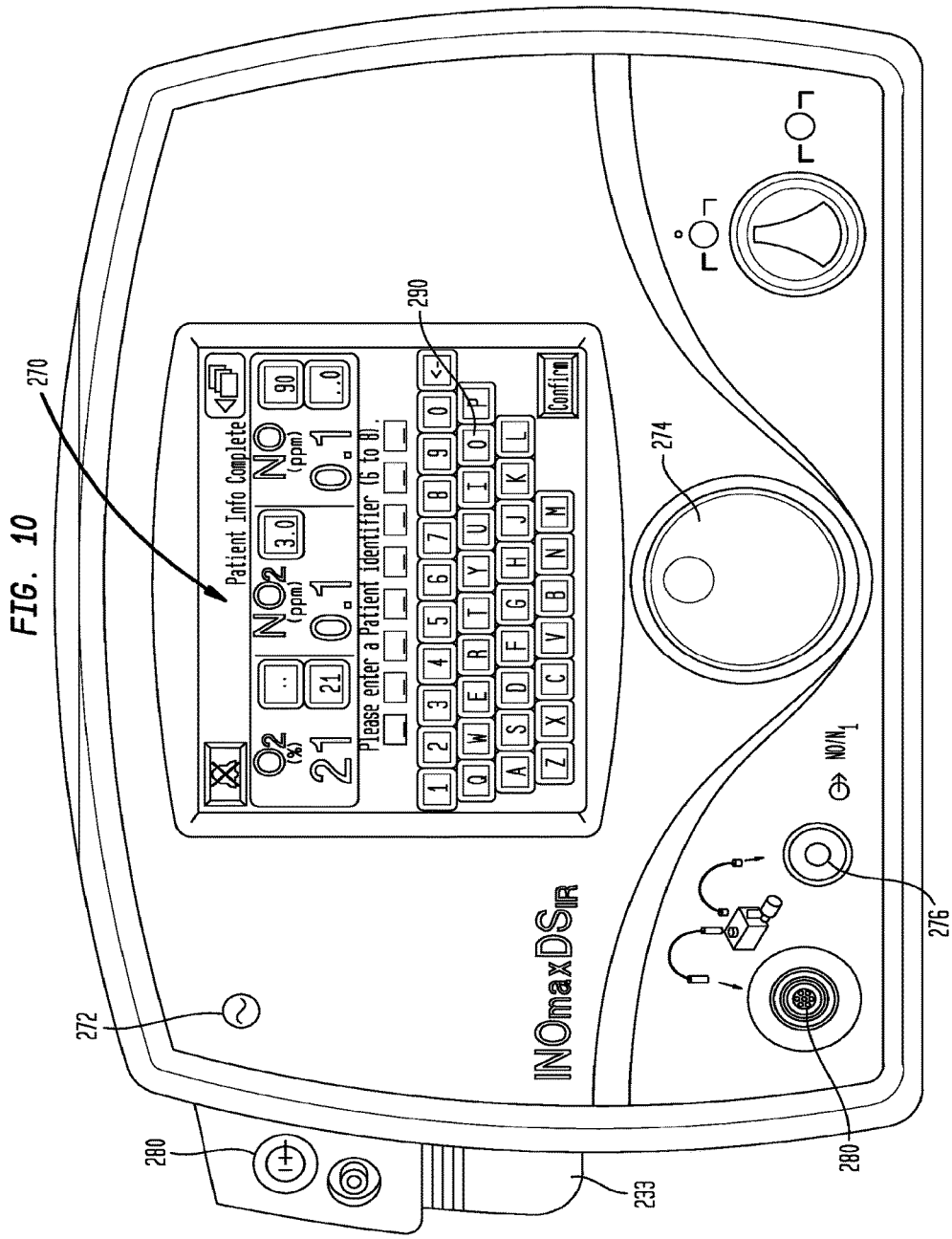
FIG. 10 illustrates a front view of a control module according to one or more embodiments.
Figure 11:
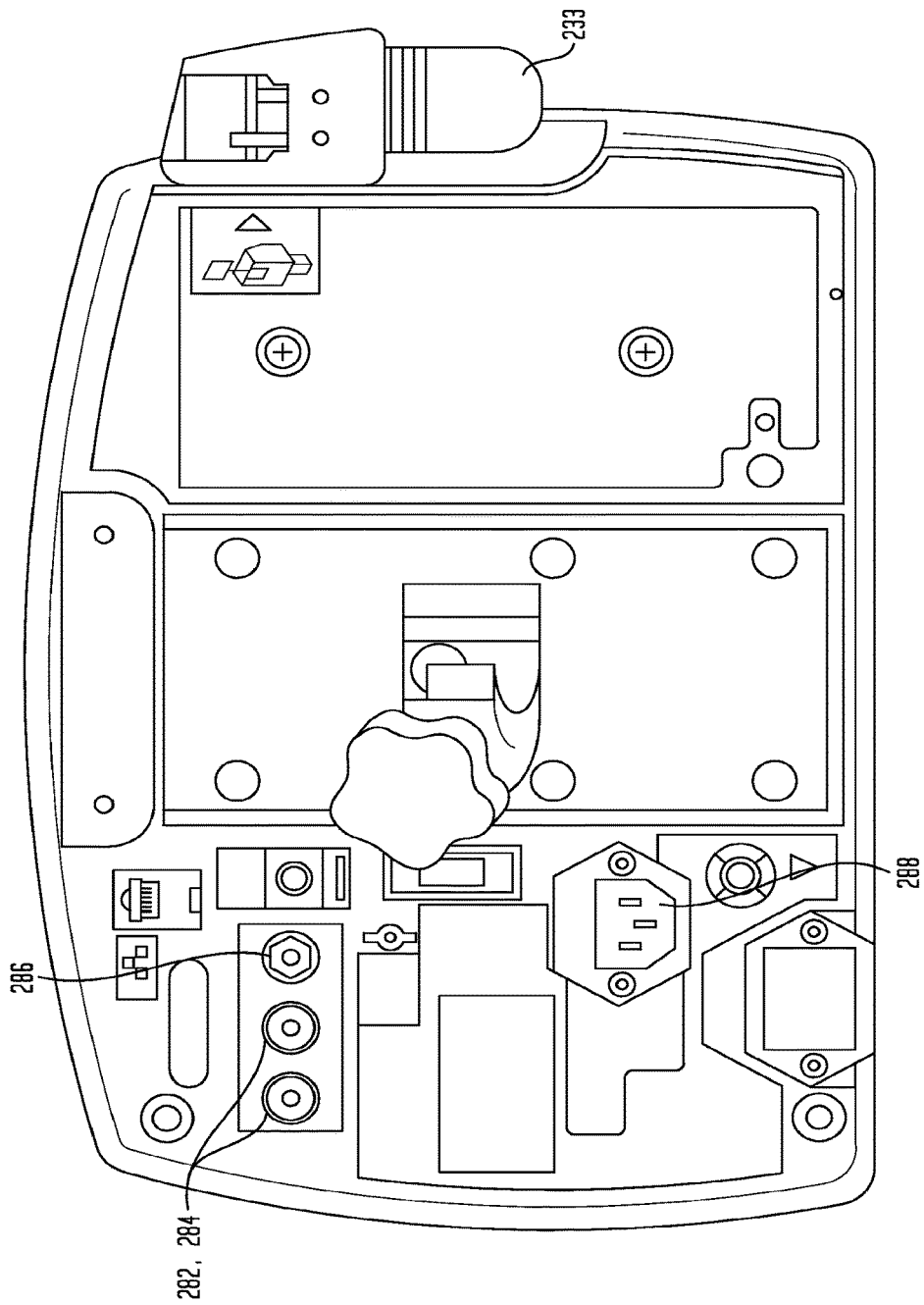
FIG. 11 illustrates a back view of the control module shown in FIG. 10.
Figure 12:
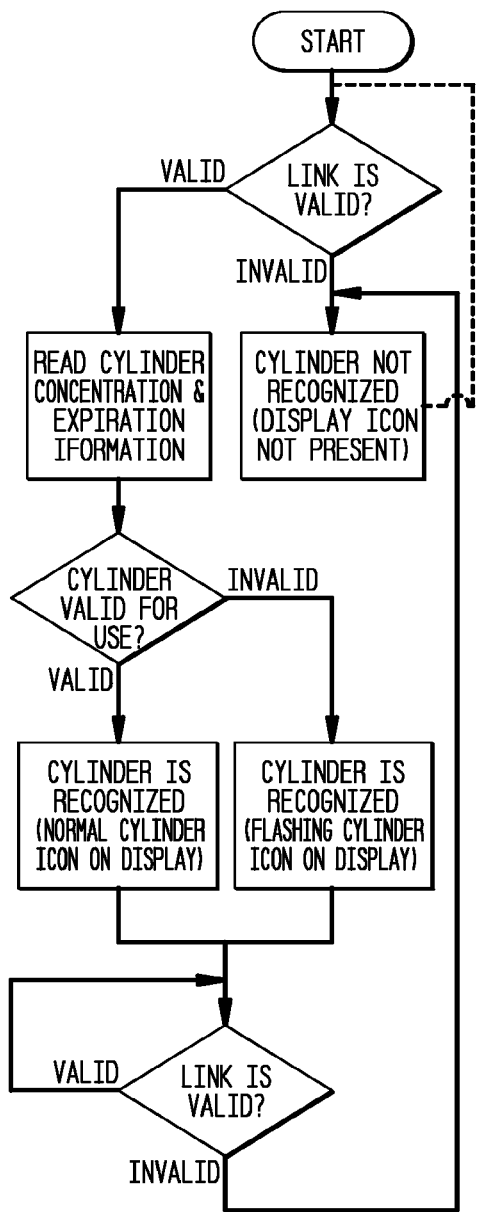
FIG. 12 is an operational flow diagram of the communication between the circuit of the gas delivery device and the control module shown in FIG. 1 regarding the gas contained within a gas source.

An exemplary control module 200 is shown in FIGS. 10-12 includes a display 270 for providing visual indication to the user the components of the gas being delivered from the gas source 50 to the ventilator 400 (e.g., NO, $O_2$, $NO_2$), the concentration of each component and whether communication has been established with one or more gas sources. Other information may also be displayed to the user. In addition, visual alarms may also be displayed on the display 270. The control module 200 may also include a main power indicator 272 indicating whether the control module is connected to a power source, such as an AC/DC power source and/or a battery. The control module 200 may also include a control wheel 274 allowing the user to navigate through various displays or information displayed on the display. An injection module tubing outlet 276 may be disposed on the control module for providing fluid communication between the delivery module 260 and the injector module 430. An injection module cable port 278 may also be provided on the control module to provide electronic communication between the delivery module 260 and the injector module 430. The control module 200 shown in FIGS. 10-12 also includes the sample line inlet 280 in fluid communication with the sample line 232 and the inspiratory limb 412 of the ventilator 400. In the embodiment shown in FIGS. 10-12, the water trap 233 is disposed on the control module, adjacent to the sample line inlet 280.

FIG. 11 illustrates a back view of the control module 200 and shows a plurality of inlets. In the embodiment shown, two gas inlets 282, 284 for connecting the control module 200 to the gas source 50 are provided and one auxiliary inlet 286 for connecting the control module 200 to an auxiliary gas source, which may include oxygen or other gas. A power port 288 is also provided on the back of the control module to connect the control module to an AC/DC power source.

The control module 200 may also include an input means 290 for allowing the user to enter patient information, for example the identity of the patient, the type and concentration of the gas and dose of the gas to be administered to the patient, the patient's disease or condition to be treated by the gas or reason for treatment, gestational age of the patient and patient weight. The input means 290 shown in FIG. 12 includes a keyboard integrated with the display. In one or more alternative embodiments, the input means may include a USB port or other port for the connection of an external keyboard or other input mechanism known in the art. The information entered via the input means 290 is stored within the CPU memory 212.

The control module 200 and the valve assembly 100 may be utilized in the gas delivery system 10 to improve patient safety. Specifically, the safety benefits of the gas delivery system described herein include detecting a non-confirming drug or gas source, an expired drug or gas, incorrect gas type, incorrect gas concentration and the like. In addition, embodiments of the gas delivery system described herein also improve efficiency of gas therapy.

Figure 13:
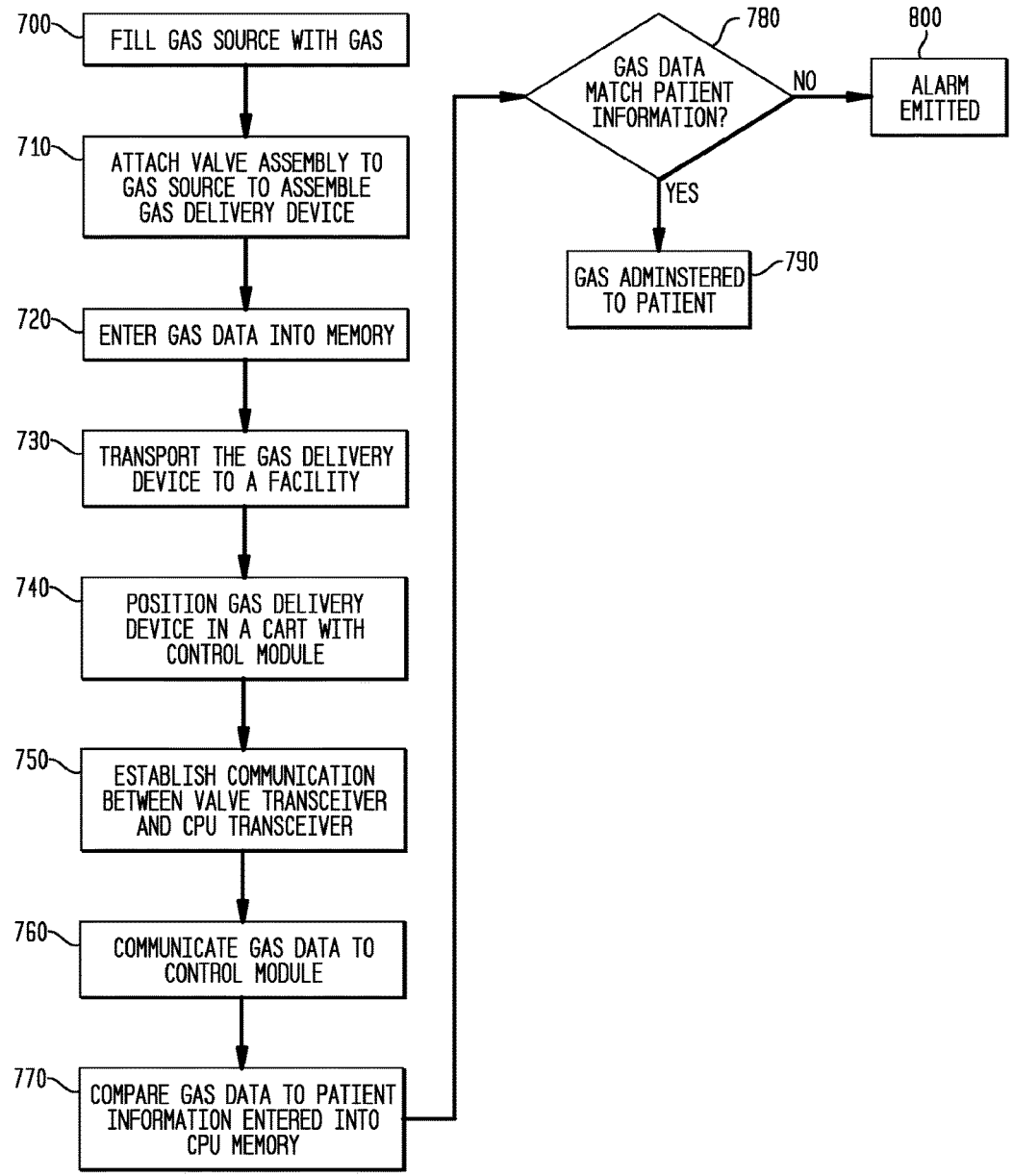
FIG. 13 is an operational flow diagram of the preparation of a gas delivery device and use within the gas delivery system according to one or more embodiments.

FIG. 13 is a block diagram showing the sequence of how gas delivery device, including the valve assembly 100, may be provided and its use within the gas delivery system 10, according to one or more embodiments. As shown in FIG. 13, the gas delivery device 10 is prepared for use by providing a gas source 50 in the form of a gas cylinder or other container for holding a gas and filling the gas source 50 with a gas (700) and attaching a valve assembly 100 as described herein, to assemble the gas delivery device 10 (710). These steps may be performed by a gas supplier or manufacturer. The gas data regarding the gas filled within the gas source 50 is entered into the valve memory 134 as described herein (720). The gas data may be entered into the valve memory 134 by the gas supplier or manufacturer that provides the gas source 50 and assembles the gas delivery device 10. Alternatively, the hospital or other medical facility may enter the gas data into the valve memory 134 after the gas delivery device has been transported to the hospital or medical facility (730). The gas delivery device 10 is positioned on a cart 500 (740) and communication between the CPU transceiver 220 and the valve transceiver 120 is established (750). The gas data stored within the valve memory 134 is conveyed to the control module 200 (760) via the wireless optical line-of-sight communication between valve transceiver 120 and the CPU transceiver 220. The CPU 210 compares the gas data to patient information entered into the CPU memory 212 (770). The patient information may be entered into the CPU memory after the gas data is entered into the CPU memory 212. The patient information may be entered into the CPU memory before the gas delivery device 10 is positioned in the cart or before communication between the CPU transceiver 220 and the valve transceiver is established. In one or more alternative embodiments, the patient information may be entered into the CPU memory 212 before the gas delivery device 10 is prepared or transported to the hospital or facility. The CPU 210 then compares whether the gas data and the patient information match (780). If the gas data and the patient information match, then gas is administered to the patient (790), for example through a ventilator or other gas delivery mechanism. If the gas data and the patient information do not match, then an alarm is emitted (800). As described otherwise herein, the alarm may be audible and emitted through the speaker 214 and/or may be visual and displayed on the display 270.

The gas delivery system described herein simplifies set-up procedures by utilizing wireless line-of-sight signals to establish communication. The user does not need to ensure all the cables are correct connected and can freely load new gas sources onto a cart without disconnecting cables linking the control module 200 and the valve assembly 100 or circuit 150. This reduces set-up time and any time spent correcting errors that may have occurred during the set-up process. The control module 200 and the circuit 150 are further designed to automatically send and detect information to establish delivery of a correct gas having the correct concentration and that is not expired. In one or more specific embodiments, such automated actions prevent the use of the gas delivery system by preventing gas flow to a patient, without user intervention.

In one or more embodiments, after communication between the valve transceiver 120 and the CPU transceiver 220 is established, the valve processor 122 includes instructions to convey the gas data stored in the valve memory 134 via the valve transceiver 120 to the CPU transceiver 220.

The CPU 210 includes instructions to store the gas data received from the CPU transceiver 220 in the CPU memory. The CPU 210 also includes an algorithm that compares the gas data with patient information that is entered into the CPU memory 212. If the gas data and the patient information do not match, the CPU 210 includes instructions to emit an alarm, which may be audible, visual or both, alerting the user that the gas contained within the gas source is different from the gas to be administered to the patient. For example, as illustrated in FIG. 12, if the gas data includes gas expiration date, the CPU memory 212 includes information regarding the current date and the CPU 210 compares the gas expiration date with the current date. If the gas expiration date is earlier than the current date, the CPU 210 emits an alarm. The alarm may be emitted through one or both the speaker 214 and display 270. In one or more embodiments, the CPU 210 may include instructions that the delivery module 260 cease or prevent delivery of the gas. In one or more embodiments, the CPU 210 includes instructions to turn the backup on/off switch 269 off if the delivery module 260 commences or continues delivery of the gas. The detection of an expired gas by the CPU 210 may be stored within the CPU memory 212.

If the gas data includes gas concentration information or data, the CPU memory 212 includes information regarding the desired concentration of gas to be administered to the patient. The control module 200 may be configured to alert the user that the gas contained within a gas source has incorrect concentration or a concentration that does not match the desired gas concentration. For example, a user may enter a concentration of 800 ppm into the CPU memory 212 and this concentration is compared to the gas concentration conveyed from the valve memory 134 to the CPU memory 212. As illustrated in FIG. 12, the CPU 210 includes instructions to compare the gas concentration of the gas with the concentration entered by the user. If the gas concentration does not match the concentration entered by the user, the CPU 210 emits an alarm, which may be audible and/or visual. In one or more embodiments, the CPU 210 may include instructions that the delivery module 260 cease or prevent delivery of the gas. In one or more embodiments, the CPU 210 includes instructions to turn the backup on/off switch 269 off if the delivery module 260 commences or continues delivery of the gas. The detection of a gas with incorrect concentration may be stored within the CPU memory 212.

In one or more embodiments, the control module 200 may be configured to detect more than one valve and to detect whether more than one valve is turned on. This configuration eliminates waste because it alerts a user that both valves are turned on and thus unnecessary gas is being delivered to via the delivery module 260. In addition, such a configuration improves safety because it avoids the issues related to having two regulators pressurized at the same time and connected to the delivery module 260. In one or more embodiments, the cover portion 225 of the control module 200 may include a second CPU transceiver 222 and the CPU 210 may include instructions for the second CPU transceiver 222 to detect wireless optical line-of-sight signals from a second valve assembly 101, and more specifically, a second valve transceiver 121. The CPU 210 may also include instructions that once a second valve assembly 101 is detected by the CPU transceiver 222, whether both valve assemblies 100, 101 are opened or have a valve status that includes an open position. In operation, a first valve assembly 100 includes a circuit with a valve processor with instructions to covey an open or closed position via the first valve transceiver 120. The circuit of the second valve assembly similarly includes a valve processor with instructions to convey an open or closed position via a second valve transceiver 121. The first CPU transceiver 220 and the second CPU transceiver 222 detect the valve statuses for each respective valve assembly from the first valve transceiver 120 and the second valve transceiver 121 via the wireless optical line-of-sight signals sent by both transceivers. The CPU 210 instructs the CPU transceivers 220, 222 to collect the valve statuses for both valve assemblies 100, 101 and the memory to store the valve statuses. The CPU 210 then compares the valve status information from the first valve assembly 100 and the second valve assembly 101 and, if the valve statuses both comprise an open position, the CPU 210 emits an alarm. The alarm may be audible and/or visual. In one or more embodiments, the CPU 210 may include instructions that the delivery module 260 cease or prevent further delivery of gas through either the first valve assembly or the second valve assembly. In one or more embodiments, the CPU 210 includes instructions to turn the backup on/off switch 269 off if the delivery module 260 commences or continues delivery of gas. The detection that more than one valve assembly had a valve that was turned on or had a valve status including an open position may be stored within the CPU memory.

In one or more embodiments, the control module 200 may be configured to alert a user when the desired dose has been delivered. In such embodiments, the patient information entered into the CPU memory 212 may include dosage information or the dose to be delivered to a patient. The valve processor 122 may include instructions to convey gas usage information from the valve memory 134, including the amount of gas delivered, to the CPU memory 212 via the valve transceiver 120. Alternatively, the valve processor 122 may include instructions to covey the duration of time the valve 170 has been turned on or has a valve status including an open position to the CPU memory 212 via the valve transceiver 120. The CPU 210 may include instructions to compare the dosage information entered by the user and stored within the CPU memory 212 with the gas usage information. The CPU 210 may include instructions to emit an alarm when the dosage information and the gas usage information match. The CPU 210 may include instructions to emit the same or different alarm to alert the user to turn off the valve or, more specifically, the actuator 114 when the dose has been delivered. In one or more embodiments, the CPU 210 may include instructions that the delivery module 260 cease or prevent further delivery of gas. In one or more embodiments, the CPU 210 includes instructions to turn the backup on/off switch 269 off if the delivery module 260 commences or continues delivery of gas.

In addition, the control module 200 may be configured to alert the user that a detected valve is and remains closed and no gas is being delivered to the patient. This configuration expedites treatment time and increases efficiency for the hospital. In such embodiments, the valve processor 122 may include instructions for the valve transceiver 120 to convey the valve status to the CPU 210 via a wireless optical line-of-sight signal. The CPU 210 includes instructions to collect the valve status information and emit an alert if the dosage information is set or other input has been entered into the CPU memory 212 to commence treatment and the valve status includes a closed position.

The control module 200 may be configured to alert the user that no valve assembly or gas source has been detected. In such embodiments, the CPU 210 includes instructions to detect the presence of a wireless optical line-of-sight signal from another transceiver, for example, the valve transceiver 120. The CPU 210 may include instructions to emit an alarm if the dosage information or other input to commence delivery of the gas has been entered into the CPU memory 212 and no signal from another transceiver has been detected. Similarly, the control module 200 may be configured to emit an alarm if communication between one or both of the CPU transceiver(s) 220, 222 and one or both of the valve transceivers 120, 121 has been lost during gas delivery. In such embodiments, the CPU 210 may include instructions to continuously detect the presence of a signal from another transceiver and emit an alarm if the dosage information or other input to commence delivery of the gas has been entered into the CPU memory 212 and no signal from another transceiver has been detected.

The CPU 210 may include instructions to alert a user when sensors in the control module 200 must be calibrated to ensure accurate delivery of gas to a patient. In addition, the CPU 210 may include instructions to correlate gas usage information from the circuit 150 of the valve assembly 100 to the patient information entered into the CPU memory 212. The CPU 210 may also have instructions to store the correlated gas usage information and the patient information in the CPU memory 212. The valve processor 122 may also include instructions detect patient information from the CPU memory 212. Specifically, the valve processor 122 may include instructions to collect patient information via the valve transceiver 120 from the CPU transceiver 220 and store the collected patient information in the valve memory 134. In such embodiments in which information from the CPU 210 is collected and stored in the valve memory 134, the CPU 210 may include instructions that the patient information and/or correlated patient information and gas usage information be conveyed from the CPU memory 212 via the CPU transceiver 220 to the valve transceiver 120. The valve processor 122 may also include instructions to correlate gas usage information with the collected patient information and store the correlated gas usage information and collected patient information in the valve memory 134. Alternatively, the valve processor 122 may include instructions to collect the correlated patient information and gas usage information from the CPU 210. The correlated information may be utilized to bill the user according to patient. In addition, the correlated information may be utilized as patient demographic data, which can assist hospitals or other facilities to generate budget reports, determine usage per department, determine usage per patient diagnosis and link usage of multiple gas sources to individual patients.

A second aspect of the present invention pertains to a method for administering a therapy gas to a patient. The method includes providing a gas in a gas source. The gas source may be prepared by a supplier to contain a gas having a predetermined composition, concentration and expiration date. The method may include providing a valve assembly 100 attached to a gas source 50 to dispense the gas contained within the gas source 50 to a patient. The method may include entering gas data, which may include gas composition, gas concentration and gas expiration date, into the valve memory 134. In one or more embodiments, the supplier may enter the gas data directly into the valve memory 134. In another variant, the gas data is provided in the form of a bar code disposed on the gas source. In such embodiments, the method includes providing a scanner in communication with the data input 108, scanning the bar code to collect the gas data information and conveying the gas data to the valve memory 134 via the data input 108. These steps may be repeated for a second gas source. The gas source(s), with the valve assembly mounted thereon may be transported to a hospital or other facility for administration to a patient. The gas source(s) are then mounted onto the cart 500 and secured by the holding bracket 520 and mounting strap 530. The method includes establishing communication between the valve transceivers disposed on each valve and the CPU transceivers 220, 222. Establishing communication may include positioning the valve assembly 100 in a line-of-sight path with at least one of the CPU transceivers 220, 222. As otherwise described herein, communication may be established by instructing the valve transceivers to send a wireless optical line-of-sight signal to the CPU transceivers 220, 222. The method may include instructing the valve transceiver 120 to send a wireless optical line-of-sight signal at pre-determined intervals, as otherwise described herein.

The method may include entering patient information into the CPU memory 212. This step may be performed before or after the gas source(s) are mounted onto the cart. The method may specifically include entering patient information such as dosage information into the valve memory 134. The method includes coordinating delivery of the gas to the patient by collecting gas data from the valve memory 134 and comparing the gas data with the patient information according to an algorithm and determining if the gas data and patient information match, according to the algorithm. Coordinating delivery of the gas may include turning on the actuator 114 of the valve 107 such that gas can flow from the inlet 104 to the outlet 106. After the dose has been delivered, the method may include correlating the gas usage information and the patient information. The method may also include recording the patient information, gas usage information and/or the correlated patient information and gas usage information in the CPU memory 212 and/or the valve memory 134. In one or more variants, the method may include utilizing the patient information, gas usage information and/or correlated patient information and gas usage information to generate invoices identifying the use of the gas by individual patients.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

The invention claimed is:

1. A gas delivery device, comprising:
a control module enclosure having mounted therein a delivery module, a control module processor and a control module memory;
wherein the control module processor is configured to control the delivery of a nitric oxide gas to the delivery module, and
a first transceiver at least partially disposed outside the control module enclosure and in electronic communication with the control module processor,
wherein, prior to delivery of the nitric oxide gas, the first transceiver is configured to receive gas data from a second transceiver disposed in a valve assembly of a gas source, the valve assembly including a valve memory that stores the gas data;
wherein the control module processor is configured to evaluate the gas data to determine that the gas source meets at least one criteria;
wherein the gas data includes at least one of gas identification, gas expiration and gas concentration; and
wherein the control module processor is configured to start flow of the nitric oxide gas to a ventilator circuit if the gas data meets the at least one criteria.

2. The gas delivery device of claim 1 wherein the control module processor is a CPU.

3. The gas delivery device of claim 1,
wherein the control module enclosure is affixed to a cart and the first transceiver is disposed on a cover portion; and
wherein the cart is configured to stow the gas source underneath the control module.

4. The gas delivery device of claim 3 wherein the gas source is disposed to allow communication between the first transceiver and the second transceiver via wireless optical line-of-sight signals.

5. The gas delivery device of claim 3 wherein communication between the cover portion and the control module processor is made via a cable and/or wirelessly.

6. The gas delivery device of claim 1, further comprising:
an injector module configured to couple to a breathing circuit affiliated with a ventilator placing the injector module in fluid communication with the ventilator, and the injector module being in electrical communication with the control module processor via wired connection and/or wireless connection.

7. The gas delivery device of claim 1 wherein control module processor is configured to cause an alarm when at least one condition is identified.

8. The gas delivery device of claim 6 wherein the alarm is one of an audio alert and a visual alert presented on a display.

9. The gas delivery device of claim 1 wherein the gas data includes at least two of gas identification, gas expiration and gas concentration.

10. The gas delivery device of claim 9 wherein the gas data is gas identification and gas expiration.

11. The gas delivery device of claim 9 wherein the gas data is gas expiration and gas concentration.

12. A control module, comprising:
a control module enclosure having mounted therein a delivery module, a control module processor and a control module memory;
wherein the control module processor is configured to control delivery of nitric oxide gas;
the control module processor being electronically connected to a first transceiver at least partially disposed outside the control module enclosure and also to the control module memory;
the control module memory having stored thereon desired gas information;
wherein the first transceiver is configured to communicate with a second transceiver, disposed in a valve assembly of a gas source of nitric oxide gas, and receive via optical line-of-sight signals, prior to delivery of the nitric oxide gas, gas data associated with the gas source wherein the gas data is stored on a valve memory disposed in the valve assembly;
the gas data including at least one of gas identification, gas expiration and gas concentration;
wherein the control module processor is configured to compare the desired gas information to the gas data and determine when at least one predetermined criteria is met; and
wherein the control module processor is configured to start the inflow of nitric oxide gas to the delivery module and ventilator if the predetermined criteria is met.

13. The control module of claim 12 wherein the control module processor controls the inflow of nitric oxide by controlling a regulator connected to an outlet of the gas source.

14. The control module of claim 12 wherein an alarm alerts when at least one condition is identified.

15. The control module of claim 14 wherein the alarm is one of an audio alert and a visual alert presented on a display.

16. The control module of claim 12 wherein the gas data includes at least two of gas identification, gas expiration and gas concentration.

17. The control module of claim 12 wherein the gas data is gas identification and gas expiration.

18. The control module of claim 12 wherein the gas data is gas expiration and gas concentration.

* * * * *